United States Patent [19]

Erlich-Deguemp

[11] 4,202,097
[45] May 13, 1980

[54] PROCESS AND DEVICE FOR RETAINING A PROSTHETIC ELEMENT ON AN OSSEOUS PART

[76] Inventor: Jean-Antoine Erlich-Deguemp, 20 rue de Vintimille, 75009 Paris, France

[21] Appl. No.: 772,999

[22] Filed: Feb. 28, 1977

[30] Foreign Application Priority Data

Feb. 27, 1976 [FR] France ................. 76 05598

[51] Int. Cl.² ........................... A61C 13/00
[52] U.S. Cl. ................................... 433/189
[58] Field of Search ............... 32/2, DIG. 6, 5, 10 A

[56] References Cited
U.S. PATENT DOCUMENTS

| | | | |
|---|---|---|---|
| 733,320 | 7/1903 | Griswold | 32/5 |
| 866,304 | 9/1907 | Roach | 32/5 |
| 2,745,180 | 5/1956 | Kiernan, Jr. | 32/10 A |
| 2,854,746 | 10/1958 | Lester et al. | 32/2 |
| 2,857,670 | 10/1958 | Kiernan, Jr. | 32/10 A |
| 2,880,508 | 4/1959 | Lester et al. | 32/2 |
| 3,514,859 | 6/1970 | Peterson | 32/2 |

FOREIGN PATENT DOCUMENTS

| | | | |
|---|---|---|---|
| 2430667 | 1/1976 | Fed. Rep. of Germany | 32/2 |
| 1569083 | 3/1969 | France | 32/2 |

Primary Examiner—Louis G. Mancene
Assistant Examiner—John J. Wilson
Attorney, Agent, or Firm—Finnegan, Henderson, Farabow, Garrett & Dunner

[57] ABSTRACT

A prosthetic element such as a dental prosthesis, is retained in position by a magnetic device which is attached to a seating or foundation structure which is permanently fixed, preferably by keying, in a cavity in the bone. The magnetic element may be releasable from the seating or foundation structure.

18 Claims, 22 Drawing Figures

PROCESS AND DEVICE FOR RETAINING A PROSTHETIC ELEMENT ON AN OSSEOUS PART

The present invention concerns a process and a device for ensuring the retention of a prosthetic element on a bony (osseous) part, more particularly a dental prosthesis adaptable removably to the maxillary bone.

It is known that the fitting in position and retention of a prosthetic element and, moreover, a removable dental prosthesis, poses numerous problems related on one hand to the morphology and the physiology of the maxillary bones and on the other hand to the function of the said prosthesis.

Indeed, removable dental prostheses must be maintained in place satisfactorily to permit the wearer of the prosthesis to speak and chew food; moreover, they must be capable of being alternately taken out and replaced to ensure their cleaning as well as the care of the mouth cavity.

The traditional mechanical cup fittings, springs or special projections, as well as sometimes causing painful pressure on the mucous membranes, are not very effective and are poorly tolerated.

Furthermore a well known disadvantage of these traditional prostheses is their poor retention, a disadvantage which becomes worse with time.

In an attempt to remedy this disadvantage, it has been proposed to fix prosthetic implants in the bony foundation constituted by the bone. Such a technique, however, necessitates the traversal of the mucous membrane and the retention in the latter of fixing elements which risks the introduction of microbe infections and the irreparable destruction of the bony foundation.

However, recently a solution has been proposed which affords numerous advantages and which consists in the retention of the prosthetic element by means of magnetic forces produced by magnetic systems disposed partly under the mucous of the dental foundation and partly in the prosthetic element.

This technique has the advantage of not creating any permanent lesion in the mucous, simplifying the construction of the prostheses and making them moreover more aesthetically attractive and less disagreeable for the wearer, as well as allowing improved retention compared with that obtained by traditional devices.

The present invention is concerned with these new techniques which it aims to perfect to render them even more efficacious.

With this in view the invention envisages improvements applicable on one hand to the structure of the part of the magnetic device which is associated with the maxillary bone and on the other hand to the means of insertion of that part of the device in the bony part which must be the most dense and the least evolutive.

Indeed, one of the problems posed by the new technique prior to the invention lay in the positioning of the magnetic device associated with the bone and in the necessity of doing this in such a way it is keyed to the bone so as to avoid displacement of the magnetic element associated with the bone as a result of force exerted on the prosthetic element pressing the latter onto the mucous, which can give rise to distress to the wearer if not lesions of the mucous leading to rejection of the device. Now this type of force exerted on the prosthetic element is fairly frequent since one has to be able to remove the prosthetic element for the purpose of frequent cleaning.

Thanks to the measures envisaged by the invention it is ensured that once put in place the magnetic device cannot be displaced relative to the bone.

With this in view the invention, according to a general aspect, concerns a process for implanting a magnetic device in a bony part for the purpose of ensuring the retention of a prosthetic element, this process being characterised in that, after incision and drawing apart of the mucous there is inserted in a cavity made in the bony part a foundation or seating structure with which is associated a magnetic element, the said seating structure being made fast with the bony part. Preferably the joining of the seating structure with the bone is effected by hooking of a part of the seating structure in the bone to avoid any pulling out after it has been put in place.

Moreover, although non-removable fixing of the magnetic element thus obtained may be effected after it has been put in place, whether by mechanical fixing of the magnetic element to the seating structure or by reconstitution of the bone itself around the magnetic element, it is envisaged according to a particular aspect of the invention, that the magnetic element preferably associated removably with the seating or foundation structure.

Such a preferred arrangement permits, among other things, eventual replacement of the magnetic element without the necessity of touching the bone again.

According to another aspect of the invention, arrangements are furthermore envisaged such as to facilitate the insertion of the seating structure and avoid the development of local stresses at the bone surface due to the attractive forces developed by the magnetic elements.

For the insertion of the seating structure these arrangements consist in the preparation of a cavity in the bony part such that its section at the level of the bottom of the cavity is greater than its entry section at the external surface of the bony part, in the introduction of the seating structure in the cavity and the spreading out in the interior of the cavity of at least one part of the seating structure in such a way that at least one of the dimensions of the spread-out structure is greater than at least one dimension of the entry section of the cavity, to achieve thereby the retention of the seating structure in the cavity.

The invention concerns also a magnetic device for carrying out the process so as to ensure the retention of a prosthetic element, particularly a dental prosthesis, on a bony part, notably the maxillary bone, this device being adapted to be lodged in a cavity formed in the bone and comprising:

a seating structure having means for keying in the cavity after its introduction into the latter, at least one magnetic mass, or a mass susceptible to magnetic attraction, associated with the seating structure, and means for ensuring the retention of the mass on the structure; these means being capable of providing the attractive forces developed by the magnetic mass itself, and/or mechanical retaining devices with which the seating structure may be provided.

The seating structure may be formed with different shapes and particularly may be constituted by a small plate, in particular of soft iron, capable of presenting a retracted position permitting its introduction into the cavity of the bone and an extended position ensuring its engagement in the cavity; in this case, the magnetic mass constituted by a permanent magnet will itself ensure its retention against the seating structure.

According to another embodiment, the seating structure will be formed by a casing having a seat adapted to receive the magnetic mass and means for locking the casing in the cavity of the bone.

It will be noted immediately that the casing once put in place in the cavity of the bone is adapted to remain therein permanently forming thus a key with the bone by means of scar tissue.

On the contrary, the magnetic mass will preferably be removably fitted in the said casing; upon the first surgical operation it is then possible to fit the casing in position in the cavity without the magnetic mass, the latter being inserted in the casing afterwards. In this way, the magnetic mass is spared almost all the operations, thereby avoiding the risk of damage or contamination of the magnetic mass.

Moreover, thanks to this arrangement, it will be convenient eventually to withdraw only the magnetic mass for its replacement by another if the need for this arises.

There will now be described, by way of non-limiting example, some embodiments of the invention, with reference to the appended drawings in which:

FIG. 4b is a view according to the arrow IVb of FIG. 4a;

Figures 1, 2, 2A:
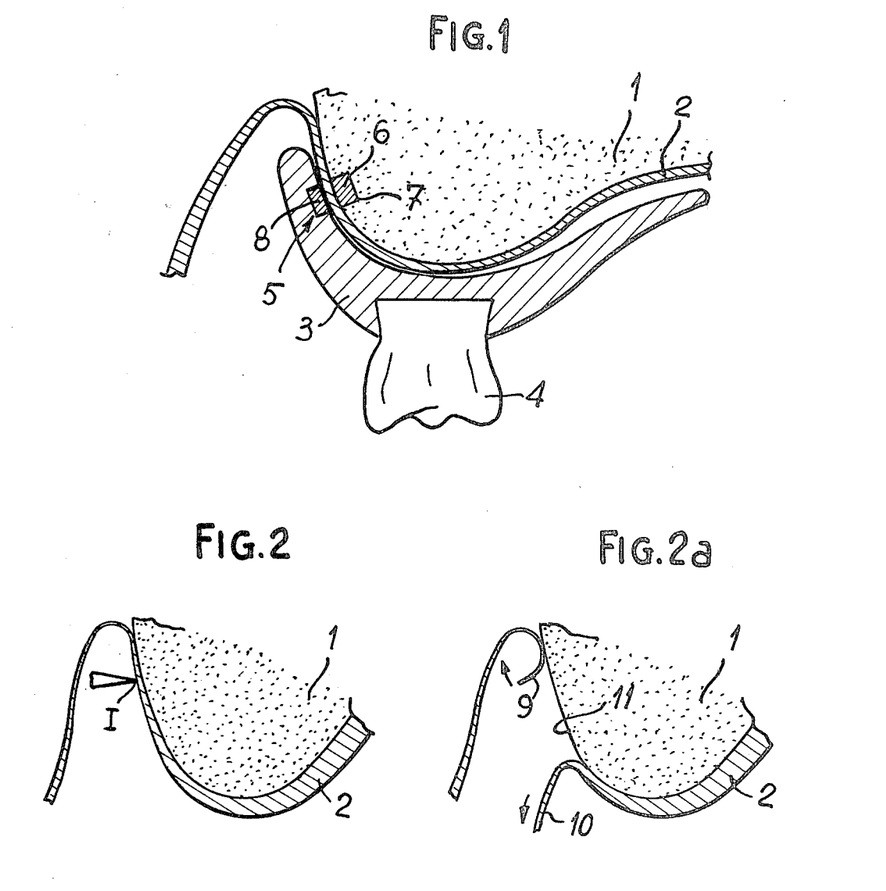
FIG. 1 is a schematic frontal view of a prosthetic system according to the invention, fitted on the upper maxillary bone.
FIGS. 2 and 2a show in front elevation the stages of incision and of lifting of the mucous in order to expose the bone.
Figure 3:
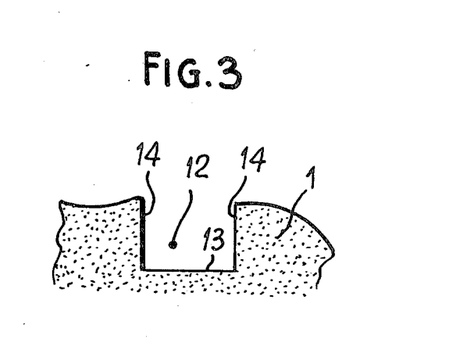
FIG. 3 is a section on an enlarged scale showing a cavity profile formed in the bone.

In FIG. 1 there is represented, in a schematic manner, a partial frontal section of the upper maxillary bone 1, having its mucous 2, on which is fitted a dental prosthesis comprising a base-plate 3 carrying artificial teeth 4.

According to the invention, the retention of the base-plate in position on the bone is effected by a magnetic device designated generally by 5, comprising a magnetic mass such that a magnet 6 placed in a cavity 7 of the maxillary bone and an opposed magnetic mass 8 (which may perhaps be a magnet or a body susceptible of being magnetically attracted) which is fixed to the base-plate 3.

Naturally, it is understood that in the case of a complete palatine base-plate, for example, the prosthesis will be maintained by at least two magnetic devices 5 situated on both sides of the jaw.

The base-plate 3 will not be described in detail, nor will the magnetic mass 8, which are considered as known.

Firstly, the present invention relates to the structure of the magnetic device 6 placed in the maxillary bone and in the same way to the process for its inclusion, the description which follows concerning these two points more particularly.

There will be first described, with reference to FIGS. 2, 2a, 3, 4, 4a and 4b, the manner in which the cavity in the maxillary bone is prepared in order to receive the magnetic device 6. As can be seen in FIG. 2, after having incised at I the mucous 2 remote from the locality where the cavity is to be formed, the mucous parts 9 and 10 are widely spread apart (FIG. 2a) to expose a surface 11 of the maxillary bone sufficient for the formation of the desired cavity.

There is then made in the maxillary bone (FIG. 3) a rough cavity shape 12 having a flat base 13 and vertical walls 14. This rough cavity may be formed by a traditional head fitted to a drill, or by a chisel.

Figure 4:
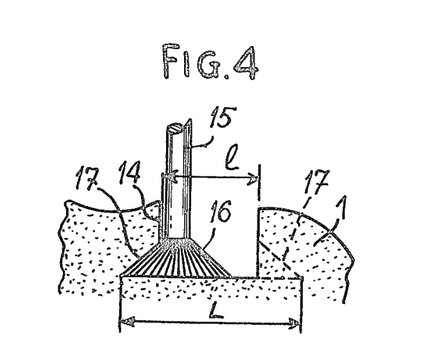
FIG. 4 shows the formation of extensions in the cavity intended to serve for support of the seating structure to prevent its extraction.

Upon completing the formation of the rough cavity extensions 17 of the cavity, at least in the two opposite walls 14 of the latter, are formed, as shown in FIG. 4, by, for example, a head 15 having an inverted cone bit 16. There is then obtained a cavity such as that shown in FIGS. 4a and 4b.

Figure 4A:
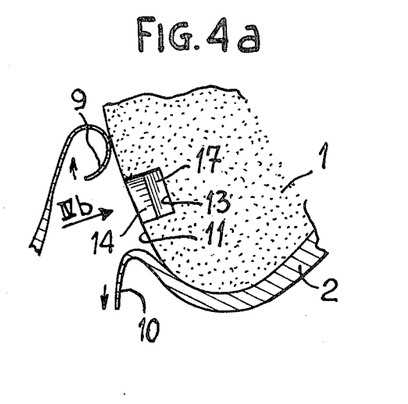
FIG. 4a is a sectional view similar to FIG. 2 showing the cavity formed in the bone.
Figure 4B:
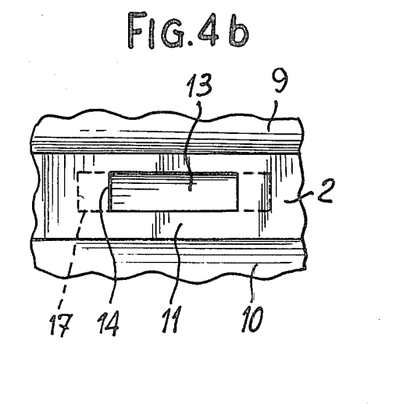

Given that the extensions 17 of the cavity have an upper inclined face, it will be understood that they may have totally different appropriate forms without departing from the invention. In the same way, it will be understood that the extensions 17 may be formed over the entire periphery of the cavity if necessary.

The length "L" of the cavity measured to the extremes of the extensions 17 is greater than the length "l" measured across the mouth of the cavity. By this means, when the magnetic device is placed in the interior of the cavity, as described later, good retention of the magnetic device is obtained.

Some embodiments of a magnetic device 6 intended to be inserted in the cavity of the maxillary bone will be described. As has been indicated above, the essential idea of the invention is the provision of a magnetic device in two parts, that is to say on the one hand a seating structure which will be inserted in the cavity and destined to remain there permanently, and on the other hand, a magnetic mass or a magnetisable mass which can be associated with the seating structure, either in a removable manner or in a non-movable manner.

Figure 5:
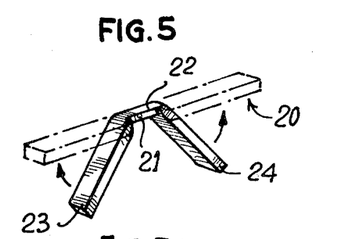
FIG. 5 represents in perspective a first embodiment of a seating structure according to the invention.

Referring to FIG. 5, there has been shown a seating structure of particularly simple form since it consists solely of a small bar of soft iron designated generally by 20 which is reduced in section in its median part at least at 21 through its thickness and, eventually, also at 22 along its width in a manner permitting folding of the bar into the deformed shape of FIG. 5, the branches 23 and 24 situated on opposite sides of the reduced section forming a "V." It is understood that the waisted central portion permits spreading of the branches 23 and 24, permitting the restoration of the bar to the rectilinear form represented in broken outline in FIG. 5.

This bar 20 is intended to be engaged in the folded form in a manner permitting its introduction into the cavity of the bone. Indeed the length "l1" (see FIG. 5a) of the folded bar will be less than the length "l" of the cavity.

Figure 5A:
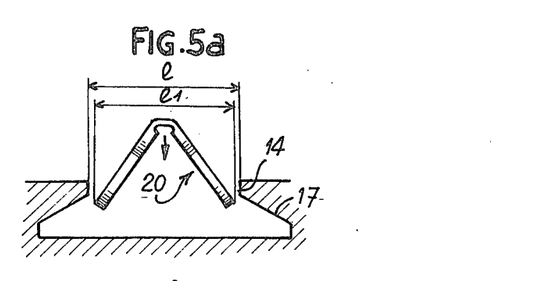
FIGS. 5a and 5b show schematically the fitting in place of the seating structure of FIG. 5 in the cavity of the bone.

Once introduced into the cavity in the manner represented in FIG. 5a it will suffice immediately to introduce the magnet 25 (see FIG. 5b), exerting on the latter a vertical force in the direction of arrow F to cause the opening of the bar 20 and its return to the rectilinear position in which the total length "l2" is greater than the length "l" of the cavity. In this way the bar becomes keyed in the cavity and cannot be withdrawn again, as represented in broken outline in FIG. 5b.

Figure 5B:
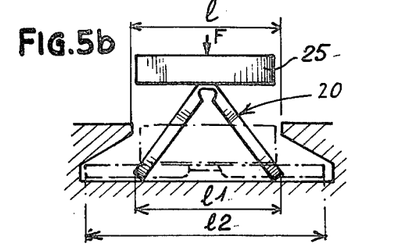

Moreover, the maintenance in place of the magnet in the cavity is effected simply by contact with the bar 20 of soft iron, as represented in broken outline in FIG. 5b.

This embodiment of a device according to the invention is however not preferred since there is a risk that the reconstitution of the bone will permanently trap the magnet 25 in the cavity and prevent its eventual withdrawal should this be necessary.

This is why it is preferred, in the following embodiments, to provide a seating structure having a housing for the magnet which separates the latter from the bone and ensures perfect removability of the magnet. In this respect the seating structure shown in FIGS. 5c and 5d constitute an interesting variant.

Figure 5C:
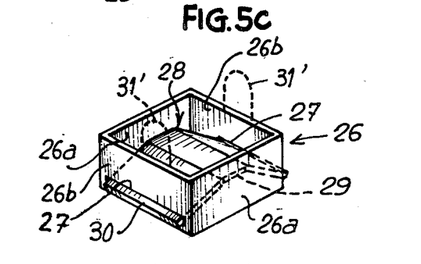
FIG. 5c represents in perspective a second embodiment of a seating case structure according to the invention.

The seating structure comprises a casing indicated generally by 26 constituted by four walls 26a and 26b opposed in pairs, this casing being open at the top and bottom.

In two opposed walls, for example 26b, of the casing, there are provided slots 27, and a small bar indicated generally by 28 of structure generally similar to the bar 20 of FIG. 5 is inserted into the interior of the casing. This bar 28 has a central part of reduced cross-section, for example, reduced thickness 29, allowing it to adopt a first stable shape in the form of a "V," as seen in FIG. 5c, as a result of which the ends 30 of the bar are engaged in the slots 27 without, however, projecting outside the casing.

Figures 5D, 5E, 5F, 5G, 5H:
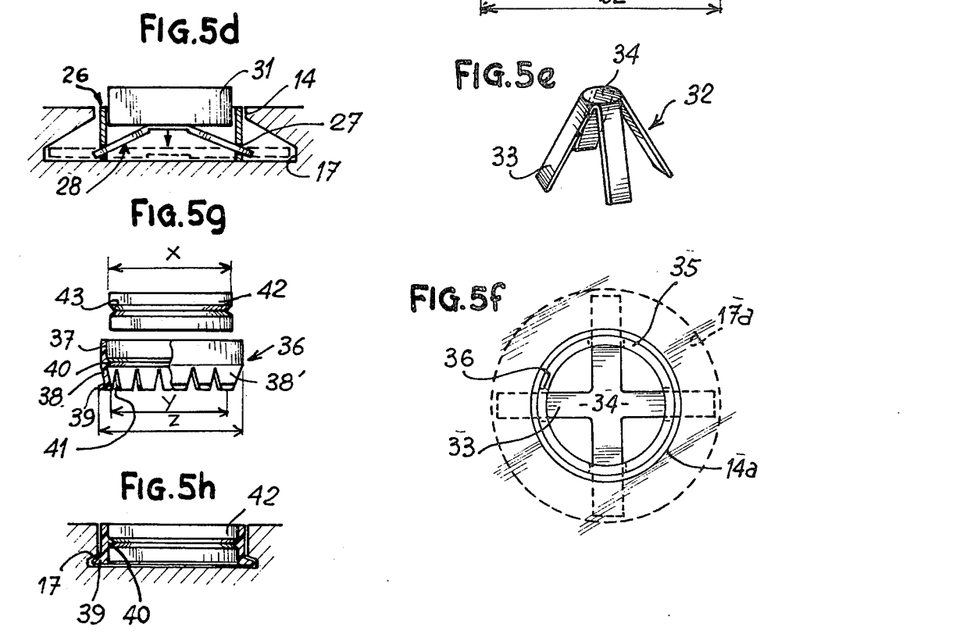
FIG. 5d shows the device of FIG. 5c placed in the cavity of the bone.
FIGS. 5e and 5f represent a third embodiment of a device of the invention.
FIGS. 5g and 5h represent a fourth embodiment of a device of the invention.

Having inserted the casing 26 in place in the cavity 14 of FIG. 5d it suffices to introduce the magnet 31 into the interior of the casing, the magnet thereby exerting a vertical force on the reduced thickness part 29 of the bar. The latter is thereby extended, being guided by the slots 27 so as to cause its projection beyond the exterior of the casing into the extensions 17 of the cavity 14. This position of the bar 28 is indicated in broken outline in FIG. 5d and causes keying of the device in the interior of the cavity.

If desired, the retention of the magnet in the casing can be completed by mechanical means constituted for example by small tabs 31' (represented in broken outline in FIG. 5c) extending from at least two opposite walls of the casing, once the latter has been engaged in the casing.

FIGS. 5e and 5f illustrate a third embodiment which utilizes an annular casing 35 adapted to be inserted in place in a cavity which, in this example, is a circular cavity 14a having a peripheral radially outward extension 17a at its base.

Slots 36, for example four in number, are formed in the casing 35 and are adapted to cooperate with a cruciform bar designated generally by 32 in FIG. 5e. This bar has a central zone 34 from which there extends four arms 33 which together lie on the surface of a conical surface.

The material used for the fabrication of the bar is at least partially malleable so as to allow the exertion of a force on the central part 34 to cause squashing resulting in extension of the arms 33 which then become engaged in the interior of the extension 17a of the cavity 14a. The bar 32 for its part may advantageously be made of soft iron or, if desired, of plastics material.

In the case where the bars 28 or 32 are made of plastics material, or in a more general manner, of a magnetic material, it will naturally be necessary to provide mechanical means for the holding of the magnet in its casing, for example by the provision of tongues or ears of the type indicated in 31' in FIG. 5c. Naturally, in this case, the casings 26 and 35 could also be made of plastics material.

In the embodiment of FIGS. 5g and 5h, the foundation or seating structure is formed by a simple ring of plastics material, generally indicated by 36, one part of which 37 is cylindrical and the lower skirt 38 of which is of conical form converging towards the axis of the ring 36. This skirt 38 is formed by a series of teeth 38' separated one from another by gaps 41, this arrangement allowing an expansion or a retraction of the skirt 38 in a manner which is in itself well known.

It will be noted that each tooth 38' presents at its base a heel 39 projecting towards the outside and intended to ensure the hooking of the ring in the bone cavity, as is more particularly seen in FIG. 5h.

Moreover, inside the ring a shoulder 40 is provided which is intended to keep in place a magnet 42 introduced inside the ring.

In its position of rest, the ring 36 presents a dimension "Z" as shown in FIG. 5g which is smaller at the opening of the bone cavity, in such a manner that it is possible to introduce the said ring in the cavity as many times as one wishes and to withdraw it without any kind of difficulty.

Moreover, the internal dimension of the ring taken at the bottom level of the teeth 38' (that is to say the dimension "y" as shown in FIG. 5g) is smaller than the corresponding dimension "x" of the magnet, so that once the ring is placed in the cavity, it is sufficient to introduce the magnet into the ring and to exert on this magnet a vertical force in order to obtain an expansion of the skirt 38 of the ring with the heels 39 engaged in the extensions 17 of the cavity made in the bone. At the end of travel, the internal shoulder 40 of the ring engages in a corresponding groove 43 provided in the periphery of the magnet 42.

In the embodiment of FIGS. 6 to 9, the casing is formed of a substantially parallelepipedic envelope 47 (see FIG. 6) which does not have an upper face.

Figure 6:
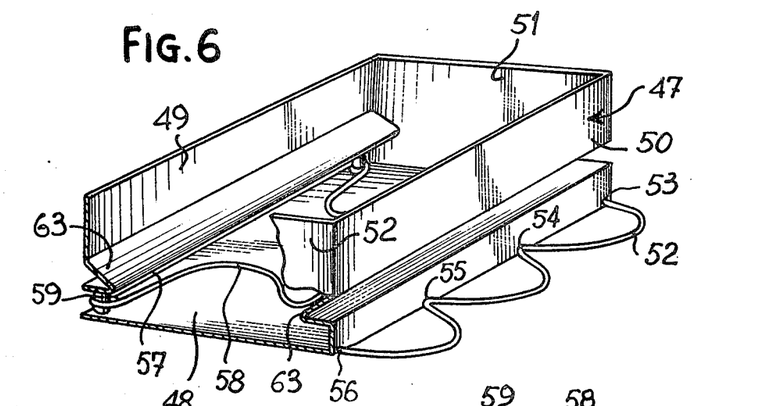
FIG. 6 is a perspective view partly cut away of a casing of a magnetic device according to another embodiment, intended to be inserted in the cavity of the bone.

This casing has a bottom 48, a front wall 49, a rear wall 50 and two lateral walls 51. The bottom 48 is prolonged, on the side of the wall 50, by a fixed projection 52 formed, for example, by a spring steel wire welded to the wall 50 at points 53, 54, 55 and 56.

Naturally, one could provide for this fixed extension, a full or perforated blade which would facilitate the formation of scar tissue.

The wall 49 has, at the level of the bottom 48, a slot 57 formed for example, by a cut-out of part of the wall.

Figures 6A, 7, 7A:
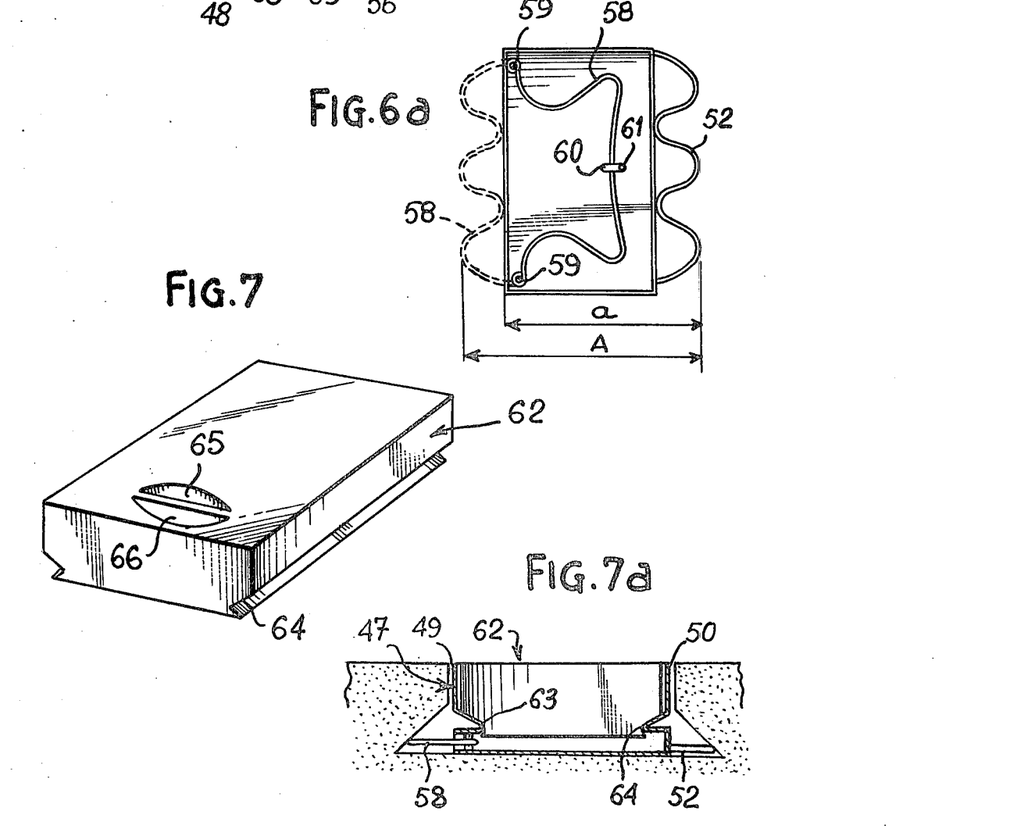
FIG. 6a is a view from below of the casing of FIG. 6.
FIG. 7 is a perspective view of a magnetic mass intended to be lodged in the casing of FIG. 6.
FIG. 7a shows the magnetic device in place in the bone cavity.
Figure 8:
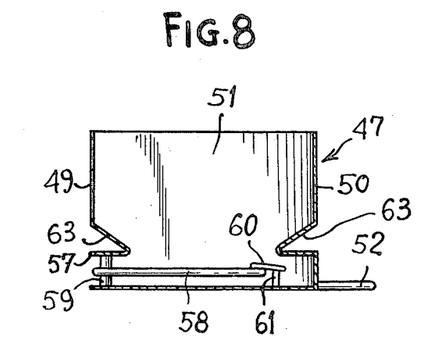
FIGS. 8 and 9 are sectional views showing the retractable projection of the casing of FIG. 6 in two positions.

The displaceable projection of the casing is formed, as can be seen particularly in FIGS. 6a, by a spring steel wire 58 the ends of which are fixed on pivots 59 rotatingly mounted in the bottom 48 of the casing.

This steel spring wire 58 is shaped so as to assume a tensioned retracted position inside the case, the form shown in FIG. 6a. The wire is kept in this retracted position by means of a system of attachments 60, formed, for example, by a hook pivotable around an axis 61. As soon as the hook 60 is opened, the freed steel wire 58 will move through the slot 59 to form a projection externally to the casing and will assume the position shown in broken lines in FIG. 6a. In this state, the spring is slackened and its form is substantially similar to that of the fixed projections 52.

As a variation, the attachment system could be formed by a simple wire which will be chopped when being used.

The dimension "a" of the casing (see FIG. 6a) is slightly smaller than at the opening of the cavity so as to permit the introduction of the casing into the cavity whereas the dimension "A" (with spread out projection) is substantially equal to the dimension "L" (FIG. 4) of the bottom of the cavity.

The walls 49 and 50 of the casing 47 present, moreover, means for ensuring the holding in place of a movable magnetic mass 62 (see FIG. 7) when the latter is placed in position in the casing after the said casing has been inserted in the cavity.

These elastically deformable retaining means permit the introduction of the magnetic mass and are formed, in the example shown, by ribs 63 provided in the walls 49 and 50 of the casing, for example, by pressing. However it will be understood that these retaining means could be formed by elastic profiles inserted inside the walls 49 and 50 and fixed, for example, by welding or any other suitable manner.

Figure 9:
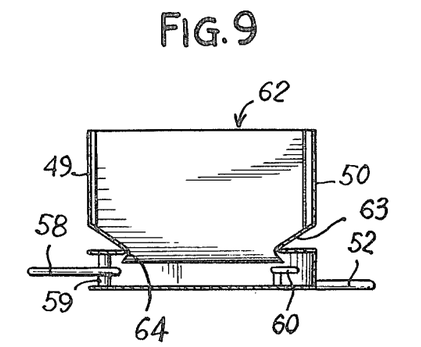

The magnetic mass 62 has at its base locking grooves 64, intended to mate with the ribs 63 of the casing (see FIG. 9).

It will be noted that in order to facilitate the holding of the magnetic mass, particularly for its extraction from the case, one would be able to provide on its upper face a cavity 65 traversed by a bridge piece beneath which the tip of an extraction instrument may be inserted.

What is claimed is:

1. An improved magnetic prosthesis-retaining device adapted for implantation in a cavity formed in an osseous part for retaining a prosthetic member having a magnetic element, the device comprising:
   (a) at least one magnetic mass;
   (b) a seating structure including keying means engageable with the wall of the cavity for firmly securing the magnetic mass seating structure fast to the osseous part, said seating structure constituted by a plate element having at least two stable positions, that is, a retracted position permitting its introduction into the cavity in the bone and an extended position for keying engagement with the bone after insertion of the plate in the bone cavity; and
   (c) means on said seating structure for retaining the at least one magnetic mass fixed thereto such that the sealing structure and the magnetic mass can be fixed against displacement relative to the osseous part.

2. Device as claimed in claim 1, characterised in that the plate element is of magnetic material, particularly soft iron, and the magnetic mass is constituted by a permanent magnet, the means for retaining the magnetic mass against the plate element being constituted by the magnetic force produced by the magnetic mass.

3. An improved magnetic prosthesis-retaining device adapted for implantation in a cavity formed in an osseous part for retaining a prosthetic member having a magnetic element, the device comprising:
   (a) at least one magnetic mass;
   (b) a seating structure including keying means engageable with the wall of the cavity for firmly securing the magnetic mass seating structure fast to the osseous part, said seating structure constituted by a casing having a housing adapted to receive the magnetic mass, said casing being elastically deformable in a transverse plane and having, in this plane, a section smaller than the corresponding section of the magnetic mass, such that the introduction of the casing into the cavity of the bone and its withdrawal are permitted when the magnetic mass is not in position in the casing, the introduction of the mass into the casing after the casing has been introduced into the bone cavity causing expansion by elastic deformation of a part of the casing and anchoring the casing in the bone cavity;
   (c) means on said seating structure for retaining the at least one magnetic mass fixed thereto such that the seating structure and the magnetic mass can be fixed against displacement relative to the osseous part.

4. Device as claimed in claim 3, characterised in that the casing is formed of plastics material and has a part constituted by elastically deformable tongues which permit expansion of the said part.

5. An improved magnetic prosthesis-retaining device adapted for implantation in a cavity formed in an osseous part for retaining a prosthetic member having a magnetic element, the device comprising:
   (a) at least one magnetic mass;
   (b) a seating structure including keying means engageable with the wall of the cavity for firmly securing the magnetic mass seating structure fast to the osseous part, said seating structure constituted by a casing having a housing adapted to receive the magnetic mass;
   (c) means for anchoring the casing after its introduction into the bone cavity, said anchoring means constituted by projections of the casing adapted to engage extensions formed in the cavity, at least one of said projections being displaceable between two positions, that is, a first position in which, when the casing is in place in the cavity, the said at least one projection is retracted and permits the introduction of the casing into the cavity, and a second position in which, after placing the casing in position in the cavity, the said projection is extended so that the dimension of the casing measured at the level of the said at least one projection is greater than that of the part of the cavity through which the casing has been introduced, thereby to effect retention of the casing in the interior of the cavity; and (d) means on said seating structure for retaining the at least one magnetic mass fixed thereto such that the seating structure and the magnetic mass can be fixed against displacement relative to the osseous part.

6. Device as claimed in claim 5, characterised in that the extension of the said at least one projection is effected by elastic means, the said projection being retracted against the action of the said elastic means.

7. An improved magnetic prosthesis-retaining device adapted for implantation in a cavity formed in an osseous part for retaining a prosthetic member having a magnetic element, the device comprising:
   (a) at least one magnetic mass;
   (b) a seating structure including keying means engageable with the wall of the cavity for firmly securing the magnetic mass seating structure fast to the osseous part, said seating structure constituted by a casing having a housing adapted to receive the magnetic mass;
   (c) means for anchoring the casing after its introduction into the bone cavity, said anchoring means constituted by projections of the casing adapted to engage extensions formed in the cavity, at least one of the projections being displaceable between two positions, that is, a first position in which, when the casing is in place in the cavity, the said at least one projection is retracted and permits the introduction of the casing into the cavity, and a second position in which, after placing the casing in position in the cavity, the said projection is extended so that the dimension of the casing measured at the level of the said at least one projection is greater than that of the part of the cavity through which the casing has been introduced, thereby to effect retention of the casing in the interior of the cavity, said at least one projection constituted by a deformable elastic wire fixed to the casing and capable of assuming two positions, namely: a retracted position within the casing, a position in which it is maintained under tension, and a position in which it projects externally of the casing and in which it is in an almost distended state; and
   (d) means on said seating structure for retaining the at least one magnetic mass fixed thereto such that the seating structure and the magnetic mass can be fixed against displacement relative to the osseous part.

8. Device as claimed in claim 7, characterised in that the elastic wire is fixed by at least one of its ends to one of the walls of the casing.

9. Device as claimed in claim 8, characterised in that the casing has an opening through which the elastic wire passes from its retracted position to its projecting position.

10. Device as claimed in claim 9, characterised in that the elastic wire is maintained under tension in the retracted position in the casing by a retaining element which is detachable to free the wire.

11. An improved magnetic prosthesis-retaining device adapted for implantation in a cavity formed in an osseous part for retaining a prosthetic member having a magnetic element, the device comprising:
   (a) at least one magnetic mass;
   (b) a seating structure including keying means engageable with the wall of the cavity for firmly securing the magnetic mass seating structure fast to the osseous part, said seating structure constituted by a casing having a housing adapted to receive the magnetic mass;
   (c) means for anchoring the casing after its introduction into the bone cavity, said anchoring means constituted by projections of the casing adapted to engage extensions formed in the cavity, said projections comprising rigid tongues on the walls of the casing; and
   (d) means on said seating structure for retaining be at least one magnetic mass fixed thereto such that the seating structure and the magnetic mass can be fixed against displacement relative to the osseous part.

12. An improved magnetic prosthesis-retaining device adapted for implantation in a cavity formed in an osseous part for retaining a prosthetic member having a magnetic element, the device comprising:
   (a) at least one magnetic mass;
   (b) a seating structure including keying means engageable with the wall of the cavity for firmly securing the magnetic mass seating structure fast to the osseous part; and
   (c) means on said seating structure for retaining the at least one magnetic mass fixed thereto such that the seating structure and the magnetic mass can be fixed against displacement relative to the osseous part, said retaining mean comprising at least one elastically deformable part of the seating structure permitting the insertion and withdrawal of the magnetic mass.

13. Device as claimed in claim 12, characterized in that the elastically deformable parts of the seating structure have male profiles projecting into the interior of the seating structure and integral with the walls of the structure.

14. Device as claimed in claim 13, characterized in that the magnetic mass has female profiles corresponding to the male profiles of the deformable part of the seating structure, the male profiles engaging in said female profiles when the magnetic mass is placed in position in the seating structure.

15. An improved method for implanting a magnetic prosthesis-retaining device in an osseous part for ensuring retention of a prosthetic member having a magnetic element, the improvement comprising the steps of:
   (a) forming a cavity in the osseous part;
   (b) inserting into the cavity a seating structure for a magnetic element;
   (c) securing the seating structure fast to the osseous part; and
   (d) fixing a magnetic element to the seating structure.

16. The improved method of claim 15 wherein step (a) comprises forming in the osseous part a cavity having a base section greater than an entrance section at the external surface of the osseous part; and wherein step (c) comprises spreading out in the interior of the cavity at least one part of the magnetic seating structure whereby at least one of the dimensions of the spread out part is greater than at least one dimension of the entrance section of the cavity for firmly securing the seating structure to the osseous part and retaining the seating structure in the cavity.

17. Process according to claim 15, characterised in that the magnetic element is connected in a removable manner to the seating structure.

18. Process according to claim 15, characterised in that the seating structure is secured to the osseous part by being keyed into the bone.

* * * * *

UNITED STATES PATENT AND TRADEMARK OFFICE
CERTIFICATE OF CORRECTION

PATENT NO. : 4,202,097
DATED : May 13, 1980
INVENTOR(S) : Jean-Antoine Erlich-Deguemp It is certified that error appears in the above—identified patent and that said Letters Patent is hereby corrected as shown below:

Claim 1(c), line 3, "sealing" should read --seating--.

Signed and Sealed this

Twenty-fifth Day of November 1980

[SEAL]

Attest:

SIDNEY A. DIAMOND

Attesting Officer

Commissioner of Patents and Trademark